USOO5723304A

United States Patent [19]
Abuknesha

[11] Patent Number: 5,723,304
[45] Date of Patent: Mar. 3, 1998

[54] IMMUNOLOGICAL DETECTION USING TWO DETECTABLE LABELS

[75] Inventor: Ramadan Arbi Abuknesha, London, United Kingdom

[73] Assignee: GEC-Marconi Limited, Stanmore, United Kingdom

[21] Appl. No.: 381,826

[22] PCT Filed: Aug. 2, 1993

[86] PCT No.: PCT/GB93/01628

§ 371 Date: Feb. 27, 1995

§ 102(e) Date: Feb. 27, 1995

[87] PCT Pub. No.: WO94/03811

PCT Pub. Date: Feb. 17, 1994

[30] Foreign Application Priority Data

| Aug. 3, 1992 | [GB] | United Kingdom | 9216465 |
| Sep. 18, 1992 | [GB] | United Kingdom | 9219743 |
| Oct. 1, 1992 | [GB] | United Kingdom | 9220722 |
| Oct. 14, 1992 | [GB] | United Kingdom | 9221578 |
| Nov. 27, 1992 | [GB] | United Kingdom | 9224897 |
| Nov. 27, 1992 | [GB] | United Kingdom | 9224898 |

[51] Int. Cl.$^6$ .............. G01N 33/53; G01N 33/542; G01N 33/537; G01N 33/543; G01N 33/554; G01N 33/551; G01N 33/546; G01N 33/552

[52] U.S. Cl. .............. 435/7.9; 435/7.1; 435/7.2; 435/7.5; 435/7.91; 435/7.92; 435/7.93; 435/7.94; 435/7.95; 435/40.5; 435/174; 435/175; 435/176; 435/177; 435/178; 435/179; 435/180; 435/181; 435/960; 435/972; 436/518; 436/523; 436/524; 436/527; 436/528; 436/529; 436/530; 436/531; 436/532; 436/533; 436/534; 436/536

[58] Field of Search .............. 435/4, 7.1, 7.2, 435/7.5, 7.9, 7.91, 7.92–7.95, 40.5, 174–181, 960, 972; 436/518, 523, 524, 527–534, 536

[56] References Cited

FOREIGN PATENT DOCUMENTS

| 0 154 916 A2 | 9/1985 | European Pat. Off. . |
| 0 154 917 A2 | 9/1985 | European Pat. Off. . |
| 0 271 974 A1 | 6/1988 | European Pat. Off. . |
| 0 310 132 A2 | 4/1989 | European Pat. Off. . |
| 0 488 195 A1 | 6/1992 | European Pat. Off. . |
| 0 538 053 A1 | 4/1993 | European Pat. Off. . |
| 2 123 146 | 1/1984 | United Kingdom . |
| WO 86/04684 | 8/1986 | WIPO . |
| WO 86/06493 | 11/1986 | WIPO . |
| WO 87/03691 | 6/1987 | WIPO . |
| WO 92/16838 | 10/1992 | WIPO . |

*Primary Examiner*—Sheela Huff
*Attorney, Agent, or Firm*—Kirschstein, Ottinger, Israel & Schiffmiller, P.C.

[57] ABSTRACT

The invention relates to a method of detection, a sensor and a test-kit which find application in immunological detection (e.g., immunoassay). The invention provides, inter alia, a method of detection, suitable for use in immunological detection of an entity, which method includes the use of a secondary species (as defined in the specification), the use of a first detectable species, and the use of a second detectable species. The method may include, for example, the use of a primary species, a secondary species, a first detectable species and a second detectable species. The primary species may be, for example, an antibody or a ligand. The secondary species may be, for example, an auxiliary species such as an auxiliary binder or an auxiliary ligand, or a species which has a part which is an auxiliary function. The entity to be detected may be an analyte species as such or may be an entity which carries or includes analytes species.

31 Claims, No Drawings

IMMUNOLOGICAL DETECTION USING TWO DETECTABLE LABELS

BACKGROUND OF THE INVENTION

The present invention relates to a method of detection, a sensor and a test-kit which find application in immunological detection (e.g. immunoassay).

SUMMARY OF THE INVENTION

According to one aspect of the present invention there is provided a method of detection, suitable for use in immunological detection of an entity, which method includes the use of a secondary species (as hereinafter defined), the use of a first detectable species, and the use of a second detectable species.

In one embodiment the present invention provides a method of detection, suitable for use in immunological detection of an entity, which method includes the use of a primary species, the use of a secondary species, the use of a first detectable species and the use of a second detectable species.

The primary species may, for example, provide a first detectable species (e.g. when the primary species is a ligand) or the primary species may be capable of being associated with a first detectable species.

The secondary species may, for example, provide a second detectable species (e.g. when the secondary species is a ligand) or the secondary species may be capable of being associated with a second detectable species. (As is further disclosed hereinafter, the secondary species may be, for example, an "auxiliary species", or may be, for example, a species which has a part which may provide an "auxiliary function").

It is to be understood that in this Specification the terms "first" and "second", as applied to detectable species, are used for the purposes of identification and do not imply any order of detection.

The present invention may find application in ratiometric detection (as is further disclosed hereinafter).

A primary species in accordance with the present invention is a species capable of taking part in a primary immune binding reaction. By way of example, a primary immune binding reaction in accordance with the present invention is one in which an entity to be detected undergoes a specific binding reaction or an authentic entity (as hereinafter defined) undergoes a specific binding reaction or an entity to be detected and an authentic entity undergo specific binding reactions. (It will be appreciated that the entity to be detected and the authentic entity undergo specific binding reactions with other species and not with each other.)

By way of example, a primary species may be a primary antibody or a ligand (e.g. an antigen).

It is to be understood that where the primary species is a ligand the primary species may be, for example, an authentic entity.

Also it is to be understood that an "authentic entity" is an entity which is capable of reacting in a substantially similar manner as an entity to be detected under substantially similar conditions. Further, it is to be understood that an authentic entity may, for example, have a chemically defined structure and/or a biologically defined, activity. It will be appreciated that an authentic entity may, for example, be used as a "standard" or a "calibrator". Where, for example, the entity to be detected is itself an analyte species (as hereinafter disclosed) the authentic entity may be an authentic analyte species (or a suitable derivative thereof) which may also be referred to as an "analyte analog".

The secondary species may be, for example, a species which does not itself take part in a primary immune reaction with an entity to be detected (or an authentic entity); such a secondary species may be regarded as an auxiliary species examples of which are auxiliary binders and auxiliary ligands.

Thus, for example, the secondary species may be an auxiliary binder comprising a binder (e.g. an antibody) for an antigenic species or a binder (e.g. a non-antibody) for a non-antigenic ligand such as a binder of a specific ligand-binder pair; an example of a binder for a non-antigenic ligand is avidin.

Examples of secondary species comprising binders for antigenic species are anti-2,4 dinitrophenol antibody, anti-fluorescein antibody, anti-digitoxin antibody, anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3,3,0] octane-2-carboxylic acid antibody, anti-endo-bicyclo [2,2,2] oct-5-ene-2,3-dicarboxylic anhydride antibody, anti-N-[4-(4-aminobenzyl)phenyl]-5-norbornene-2,3-dicarboximide antibody, and anti-[IR-(2-endo, 3-exo)]-3-hydroxy-4,7,7-trimethyl bicyclo [2,2,1] heptane-2-acetic acid antibody.

Alternatively, by way of example, the secondary species may be an auxiliary ligand comprising an antigenic species (e.g. a hapten) or a non-antigenic ligand (such as a ligand of a specific ligand-binder pair); an example of a non-antigenic ligand is biotin.

Examples of secondary species comprising antigenic species are 2,4-dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyl-3-quinaldine carboxylic acid, cis-bicyclo [3,3,0] octane-2-carboxylic acid, endo-bicyclo [2,2,2] oct-5-ene-2,3-dicarboxylic anhydride, N-[4-(4-aminobenzyl)phenyl]-5-norbornene-2,3-dicarboximide, and [IR-(2-endo, 3-exo)]-3-hydroxy-4,7,7-trimethyl bicyclo [2,2,1] heptane-2-acetic acid.

Alternatively, by way of example, a secondary species may be a species which has a part which is capable of undergoing a specific binding reaction with a secondary species reaction partner (as further disclosed hereinafter) and a part which provides a primary species (said primary species being a binder for a primary species) which is capable of undergoing a specific reaction with a primary species. It will be understood that the part capable of undergoing specific binding with the secondary species reaction partner may be regarded as an "auxiliary function". An example of a species which has a part capable of undergoing a specific binding reaction with a secondary species reaction partner and a part which is capable of undergoing a specific binding reaction with a primary species is a bifunctional antibody.

A secondary species in accordance with the present invention may be a species which is an auxiliary species which is capable of undergoing specific binding with a secondary species reaction partner. Alternatively, a secondary species in accordance with the present invention may be a species which has an auxiliary function which is capable of undergoing specific binding with a secondary species reaction partner. A secondary species reaction partner may also be considered to be an auxiliary species in that it is a species which does not itself take part in a primary reaction with an entity to be detected (or an authentic entity).

Where the primary species provides a first detectable species the primary species may provide a first detectable species at any suitable time and in any suitable manner.

Thus, for example, where the primary species is a ligand the primary species or a part of the primary species (which may be, for example, a structure comprising a chemical group or a combination of chemical groups) may be a detectable species (e.g. a detectable structure).

Alternatively, for example, where the primary species is capable of being associated with a first detectable species, the primary species may be associated with the first detectable species at any suitable time and in any suitable manner.

For example, the primary species may be associated with the first detectable species at any convenient time during the performance of a method of detection of an entity to be detected.

Also, by way of further example, the primary species may be associated directly with a first detectable species (e.g. by means of a suitable linkage such as a covalent bond).

Alternatively, by way of example, the primary species may be indirectly associated with a first detectable species. Thus, for example, the primary species may be associated with the first detectable species via one or more other species. By way of example, the primary species may be bound with an antibody for the primary species said antibody carrying a first detectable species. Where the primary species itself is an antibody it will be appreciated that the antibody thereto may be an antibody to portions of the primary species; where the primary species is an antibody, an antibody thereto may be considered to be a second antibody.

Where the primary species is associated with a first detectable species via one other species that other species may be considered to be a third species; the primary species may be linked, for example, with that third species at any suitable time and in any suitable manner.

For example, a third species may be linked directly to a primary species. Alternatively, by way of example, the third species may be linked to the primary species by means of a fourth species, said third and said fourth species being capable of undergoing a specific binding reaction such that the primary species becomes indirectly linked to the third species.

In the case of effecting a non-competitive sandwich assay the fourth species may be, for example, an entity to be detected; in such a case the third species may be considered to be a "developing" ligand or binder inasmuch as it may be applied in order to associate the first detectable species with the primary species when it is appropriate so to do.

Where the secondary species provides a second detectable species the secondary species may provide a second detectable species at any suitable time and in any suitable manner.

Thus, for example, where the secondary species is a ligand the secondary species or a part of the secondary species (which part may be, for example, a structure comprising a chemical group or a combination of chemical groups) may be a detectable species (e.g. a detectable structure).

It will be appreciated that where the secondary species is a detectable structure the secondary species and the second detectable species may be the same species.

Enzymes and species capable of giving a fluorescent signal (e.g. fluorophores) are examples of species which may be chosen so as to act both as a secondary species and as a second detectable species; thus, it is to be understood, by way of example, that an enzyme (such as those disclosed further hereinafter), or a fluorophore (such as those disclosed further hereinafter), may act as an auxiliary ligand and as a detectable species. By way of example, a fluorophore may be detected by any suitable means such as those known in the field of immunological detection; also by way of further example, an enzyme may be detected by any suitable means such as those known in the field of immunological detection.

Alternatively, for example, where the secondary species is capable of being associated with a second detectable species the secondary species may be associated with the second detectable species at any suitable time and in any suitable manner.

For example, the secondary species may be associated with the second detectable species at any convenient time during the performance of a method of detection of an entity to be detected.

Also, by way of further example, the secondary species may be associated directly with a second detectable species (e.g. by means of a suitable linkage such as a covalent bond).

Alternatively, by way of example, the secondary species may be indirectly associated with the second detectable species. Thus, for example, the secondary species may be associated with the second detectable species via one or more other species.

Where the secondary species is associated with a second detectable species via one other species the secondary species may be bound, for example, with that other species at any suitable time and in any suitable manner.

For example, the said other species may be linked directly to the secondary species. Alternatively, by way of example, the said other species may be linked to the secondary species by means of a further species.

By way of example, the secondary species may be used in bringing about attachment to a support material, attachment may be utilised for any chosen purpose; thus,for example, attachment may be utilised mainly for the purpose of providing secondary species on a support material; alternatively, by way of further example, attachment may be utilised in effecting a separation (e.g. as may be desired in an heterogeneous immunological assay). It will be appreciated that attachment to a support material may be considered to be "immobilisation".

Accordingly the secondary species may be, for example, used in bringing about attachment to a support material by reaction with a secondary species reaction partner.

Thus, for example, the present invention may include the use of a secondary species reaction partner.

The secondary species and the secondary species reaction partner may be chosen such that they may bind together by means of a specific binding reaction.

A secondary species reaction partner may be provided on a support material as is further disclosed hereinafter.

For example, where a secondary species is a binder, the secondary species reaction partner may be a ligand which may be regarded as an auxiliary ligand. By way of example, where a secondary species is an auxiliary binder, the secondary species reaction partner may be a ligand which may be regarded as an auxiliary ligand; conversely, by way of example, where the secondary species is an auxiliary ligand, the secondary species reaction partner may be a binder which may be an auxiliary binder or a binder which has an auxiliary function.

Thus, for example, where the secondary species is a binder (e.g. an antibody) for an antigenic species the secondary species reaction partner may be an antigenic species. Alternatively, by way of example, where the secondary species is an antigenic species (e.g. an antigenic ligand) the secondary species reaction partner may be a binder (e.g. an antibody) for the antigenic species. By way of further example, where the secondary species is a binder for a non-antigenic ligand (such as a binder of a specific ligand-binder pair) the secondary species reaction partner may be a non-antigenic ligand. Alternatively, by way of further example, where the secondary species is a non-antigenic ligand (such as a ligand of a specific ligand-binder pair) the secondary species reaction partner may be a binder for a non-antigenic ligand.

For example, where the secondary species is avidin, the secondary species reaction partner may be the non-antigenic ligand biotin. Conversely, where the secondary species is the non-antigenic ligand biotin, the secondary species reaction partner may be avidin.

A secondary species reaction partner may be, for example, provided on a support material in any suitable manner, and it is to be understood that in this Specification "providing on a support material" and "provided on a support material" in respect of a secondary species reaction partner embrace, for example, situations where the support material carries a secondary species reaction partner, and situations where the support material itself, or a part of the support material itself, provides a secondary species reaction partner.

Thus, for example, a secondary species reaction partner may be provided by chemical groups or units of the support material. Alternatively, a secondary species reaction partner may be, for example, attached to the support material (e.g. by covalent linkage or adsorption). Where the support material is, for example, a polymer, units of the polymer may act as a secondary species reaction partner. Also, by way of example, surface groups present on a support material, such as polystyrene or modified silica, may act as a secondary species reaction partner.

Where the secondary species reaction partner is provided by the support material itself, or a part thereof, the secondary species reaction partner may comprise a ligand. Where the secondary species reaction partner is attached to a support material the secondary species reaction partner may be a ligand or a binder.

By way of example, the support material may, if desired, provide oligomers or polymers of a secondary species reaction partner.

Where a secondary species reaction partner is attached to a support material the secondary species reaction partner may be directly attached to the support material or indirectly attached to the support material via other species (e.g. a carrier protein).

In one embodiment the present invention provides a method which also includes the step of attaching, either directly, or indirectly, a secondary species reaction partner to a support material.

By way of further example, the surface of a support material may be activated thereby to permit attachment of a secondary species reaction partner; for example, the surface of a suitable support material may be activated by chemical treatment to provide free amino groups to which a secondary species reaction partner may be linked.

Further, by way of example, an oligomer or oligomers of a secondary species reaction partner, or a polymer or polymers of a secondary species reaction partner may be attached directly or indirectly to a support material.

Thus for example, oligomers of a secondary species reaction partner or polymers of a secondary species reaction partner may be attached to free amino groups on a support material.

Also, by way of example, a secondary species reaction partner may be linked (e.g. covalently or otherwise) to a further species (e.g. a carrier protein or a polymer) and the further species may be associated with the support material such that the secondary species reaction partner may become indirectly provided on the support material.

By way of further example, it is possible to link (e.g. covalently or otherwise) oligomers or polymers of a secondary species reaction partner to a further species (e.g. a carrier protein or a polymer) and the further species may be associated with the support material such that oligomers of secondary species reaction partner or polymers of secondary species reaction partner may become indirectly provided on the support material.

Where a secondary species reaction partner is attached to a support material, attachment of the secondary species reaction partner may be effected at any desired time. Thus, for example, a secondary species reaction partner may be allowed to bind, respectively, with an appropriate secondary species before, or after, the secondary species reaction partner is attached to the support material; however, in general, it may be more convenient to attach a secondary species reaction partner to the support material before bringing together the secondary species reaction partner and a secondary species.

It is to be understood that the use of oligomers or polymers of a secondary species reaction partner may be advantageous in certain circumstances. Thus, for example, by use of an oligomer or a polymer of a secondary species reaction partner more secondary species reaction partner may be provided than it is possible to provide when using only single "units" of secondary species reaction partner. Accordingly, for example, the provision of more secondary species reaction partner offers the possibility of faster reactions since more secondary species reaction partner is available to undergo reaction, with available secondary species.

As hereinbefore disclosed examples of secondary species are binders such as anti-2,4 dinitrophenol antibody, anti-fluorescein antibody, anti-digitoxin antibody, anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3,3,0] octane-2-carboxylic acid antibody, anti-endo-bicyclo [2,2,2] oct-5-ene-2,3-dicarboxylic anhydride antibody, anti-N-[4-(4-aminobenzyl) phenyl]-5-norbornene-2,3-dicarboximide antibody, and anti-[1R-(2-endo, 3-exo)]-3-hydroxy-4,7,7-trimethyl bicyclo [2,2,1] heptane-2-acetic acid antibody, and it is to be understood that the corresponding secondary species reaction partners for these are, respectively, the antigenic species 2,4 dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyl-3-quinaidine carboxylic acid, cis-bicyclo [3.3.0] octane-2-carboxylic acid, endo-bicyclo [2.2.2] oct-5-ene-2,3-dicarboxylic anhydride, N-[4-(4-aminobenzyl) phenyl]-5-norbornene-2,3-dicarboximide, and [IR-(2-endo, 3-exo)]-3-hydroxy-4,7,7-trimethyl bicyclo [2.2.1] heptane-2-acetic acid.

Also, as hereinbefore disclosed, examples of secondary species are ligands such as the antigenic species 2,4-dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyl-3-quinaldine carboxylic acid, cis-bicyclo [3.3.0] octane-2-carboxylic acid, endo-bicyclo [2.2.2] oct-5-ene-2,3-dicarboxylic anhydride, N-[4-(4-aminobenzyl) phenyl]-5-norbornene-2,3-dicarboximide, and [IR-(2-endo, 3-exo)]-3-hydroxy-4,7,7-trimethyl bicyclo [2.2.1] heptane-2-acetic acid, and it is to be understood that the corresponding secondary species reaction partners for these are, respectively, the binders anti-2,4 dinitrophenol antibody, anti-fluorescein antibody, anti-digitoxin antibody, anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3.3.0] octane-2-carboxylic acid antibody, anti-endo-bicyclo [2.2.2] oct-5-ene-2,3-dicarboxylic anhydride antibody, anti-N-[4-(4-aminobenzyl) phenyl]-5-norbornene-2,3-dicarboximide antibody, and anti-[IR-(2-endo, 3-exo)]-3-hydroxy-4,7,7-trimethyl bicyclo [2.2.1] heptane-2-acetic acid antibody.

Where, for example, the secondary species is an enzyme (e.g. horse-radish peroxidase or alkaline phosphatase) the corresponding secondary species reaction partner may be a binder comprising an antibody to the enzyme (e.g. anti-horseradish peroxidase antibody or anti-alkaline phosphatase antibody).

By way of example, in bringing about attachment to a support material a secondary species reaction partner may be attached (directly or indirectly) to a support material and the secondary species and the secondary species reaction partner may be allowed to interact by means of a specific binding reaction thereby to bring about attachment, said secondary species thereby being attached to the support material via the secondary species reaction partner.

A secondary species reaction partner may be attached to a support material in any suitable manner and at any suitable time. For example, a secondary species reaction partner may be attached to a support material by any suitable linkage, for example, a linkage which involves a link of a non-specific binding type (e.g. a covalent linkage or adsorption). Also, by way of example, a secondary species reaction partner may be attached to a support material at any convenient time during the performance of a method of detection in accordance with the present invention.

Interaction of the secondary species and the secondary species reaction partner may be allowed to proceed in any suitable manner and at any suitable time (e.g. at any suitable time in the performance of a method of detection in accordance with the present invention).

It will be appreciated that where the secondary species is attached to another species, that species may also become (indirectly) attached to a support material.

By way of example the secondary species may be associated with one or more other species as required. Thus, for example, the secondary species may be associated with a primary species and/or a first detectable species and/or a second detectable species.

A secondary species may, for example, be associated with a primary species in any suitable manner and at any suitable time.

For example, a secondary species and a primary species may be associated in any suitable manner.

For example, the secondary species may be linked, either directly or indirectly, with a primary species reaction partner such that upon linking between the primary species and the primary species reaction partner the primary species and the secondary species become associated.

Accordingly, the present invention may, for example, include the use of a primary species reaction partner.

By way of example, the nature of the primary species reaction partner may be such that it is capable of undergoing a specific binding reaction with the primary species.

For example, where the primary species is an antigenic species, the primary species reaction partner may be an antibody for the antigenic species; alternatively, for example, where the primary species is an antibody, the primary species reaction partner may be an antigenic species for the antibody.

By way of example, a secondary species may be linked with a primary species reaction partner by means of any suitable linkage. An example of such a linkage is one which involves a link, of a non-specific binding type, to the secondary species.

An example of a link of a non-specific binding type is a covalent link. Thus, for example, the linkage may involve a covalent link to a secondary species.

Another example of a link of a non-specific binding type is a link which involves adsorption. Thus, for example, a secondary species and a primary species reaction partner may be linked by both being adsorbed on a suitable material (e.g. a carrier material such as latex particles).

As hereinbefore disclosed, a secondary species may be linked with a primary species reaction partner directly or indirectly.

Thus, for example, where a secondary species is arranged to be linked directly to a primary species reaction partner, the linkage may be a link of a non-specific binding type (e.g. a covalent linkage) between the secondary species and the primary species reaction partner.

By way of further example, where a secondary species is arranged to be linked indirectly to a primary species reaction partner, the linkage may include one, or more, other species, and one or more links as required, one of the links being a link of a non-specific binding type to the secondary species.

It is to be understood that where, for example, one or more links are involved in the linkage, and one of the links is a link, of a non-specific binding type, to the secondary species, any further link or links in the linkage may be of any suitable type (e.g. non-specific binding type or specific binding type); thus, for example, the linkage may include a further link or links of a non-specific binding type, or may include a further link or links of a specific binding type (e.g. a ligand-binder type) or a mixture of types of links (e.g. non-specific binding type and specific binding type).

Where a secondary species is linked to a primary species reaction partner via one or more other species, said other species, or one of said other species, may be, for example, a second antibody, or a ligand, or a binder and, for example, the secondary species may be covalently linked to said other species or said one of said other species.

It is to be understood that a secondary species may be associated with a primary species reaction partner by any suitable linkage; such a linkage may include a non-specific binding link or links (e.g. a covalent link or links or adsorption), or a specific binding link or links, or any combination of such links.

Further, by way of example, if desired a secondary species reaction partner may be attached to a support material and the said secondary species reaction partner may also be linked to a second detectable species. Thus, when a secondary species and a secondary species reaction partner bind together the secondary species may become associated with the second detectable species by being indirectly linked therewith.

Examples of support materials which may be used in accordance with the present invention are a solid phase material such as a reaction vessel wall, insoluble polysaccharides, microparticles (e.g. particulate microcellulose), polystyrene (e.g. in the form of wells, beads, microtitre plates, discs, sticks or tubes), cross-linked dextran (e.g. Sephadex), insoluble polymer structures, glass surfaces, derivatised silica surfaces (e.g. having silyl groups with chemical functions attached), soluble polymers attached to a suitable surface (e.g. a glass surface), microparticulate materials with entrapped ferrous oxide (magnetisable particles), nylon and. polyamides.

By way of further example, a support material may be in the form of a carrier (e.g.a tape) which may be moved from a sample application means, for applying a sample to the carrier, to a detection means thereby to allow successive (e.g. continuous) detection of entities.

It will be appreciated that some types of support materials may be inappropriate for use with some entities to be detected. Thus, for example, where the entity to be detected is a metal ion, or contains a metal, the use of some types of support materials may be inappropriate (e.g. support materials containing entrapped iron oxide may give rise to unacceptable interference).

The first detectable species and the second detectable species may be any suitable detectable species which may be utilised in the detection of an entity which it is desired to detect. It is to be understood that a detectable species may be, for example, a detectable structure.

Examples of detectable species are enzymes (e.g. alkaline phosphatase, β-galactosidase and horse-radish peroxidase), species capable of giving a fluorescent signal (e.g. fluorophores (or polymeric fluorophores)), chemiluminescent compounds, bioluminescent compounds, radioisotopes, dyes, ligands (or polymers of ligands), and binders (or polymers of binders). Examples of fluorophores are fluoresceins, coumarins and rhodamine.

By way of example, an enzyme may be detected by a corresponding substrate, fluorophores and radioisotopes may be detected directly with suitable detectors, ligands may be detected by use of binders therefor, said binders being associated with tracer species, and binders may be detected by use of ligands therefor, said ligands being associated with tracer species.

The tracer species may be, for example, any suitable tracer species such as those known in the art relating to protein binding assays (e.g. immunoassays). (It is to be understood that a tracer species may also be considered to be a signal species or a labelling species.)

Examples of tracer species are enzymes (e.g. alkaline phosphatase, β-galactosidase and horseradish peroxidase), species capable of giving a fluorescent signal (e.g. fluorophores (e.g. fluoresceins, coumarins or rhodamine)), chemiluminescent compounds, bioluminescent compounds, radioisotopes and dyes.

Detection or measurement of a signal from a detectable species or from a tracer species may be carried out in any suitable manner such as those known in the immunochemical field.

Where, for example, a ligand or a binder is used (as hereinbefore disclosed) as a detectable species any suitable ligand or binder may be utilised.

Examples of ligands are antigenic species such as 2,4 dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyl-3-quinaldine carboxylic acid, cis-bicyclo [3.3.0] octane-2-carboxylic acid, endo-bicyclo [2.2.2] oct-5-ene-2,3-dicarboxylic anhydride, N-[4-(4-aminobenzyl) phenyl]-5-norbornene-2,3-dicarboximide, and [IR-(2-endo, 3-exo)]-3-hydroxy-4,7,7-trimethyl bicyclo [2.2.1] heptane-2-acetic acid, which may be considered to be haptens, and non-antigenic ligands such as the ligand of a specific ligand-binder pair (e.g. biotin).

Examples of binders are antibodies (e.g. anti-2,4 dinitrophenol antibody, anti-fluorescein antibody, anti-digitoxin antibody and anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3.3.0] octane-2-carboxylic acid antibody, anti-endo-bicyclo [2.2.2] oct-5-ene-2,3-dicarboxylic anhydride antibody, anti-N-[4-(4-aminobenzyl) phenyl]-5-norbornene-2,3-dicarboximide antibody, and anti-[IR-(2-endo, 3-exo)]-3-hydroxy-4,7,7-trimethyl bicyclo [2.2.1] heptane-2-acetic acid antibody) and binders of a specific ligand-binder pair (e.g. avidin). It will be appreciated that antibodies to which reference is made in this Specification (e.g. antibodies such as those immediately hereinbefore disclosed) may be prepared by any suitable method such as those known for the raising of polyclonal or monoclonal antibodies; thus antibodies may be raised, for example, by immunising animals.

By way of example, by suitable choice of first detectable species and second detectable species it is possible, in accordance with the present invention, to carry out a ratiometric detection of an entity; thus, for example, a ratiometric detection may be effected.

In utilising the present invention in a ratiometric detection, the first detectable species and the second detectable species may be chosen such that they may be determined independently of each other without any unacceptable level of interference between the two detectable species.

Any suitable combination of first detectable species and second detectable species may be used; thus, for example, two fluorophores, or two enzymes, or one fluorophore and one enzyme, may be used. In some circumstances it may be desirable not to use two detectable species of the same kind; thus, for example, it may be difficult to differentiate between two radioactive detectable species and so it may be preferable to use one radioactive detectable species and one detectable species of a different kind (e.g. a fluorophore).

It will be appreciated that it is often difficult accurately to make absolute measurements of relatively low signal levels from a detectable species.

However, in immunoassays the use of very low signal levels (e.g. from detectable species such as a fluorescence tracer) is often required in order to meet conditions necessary for achieving sensitive detection of an entity.

The accuracy and precision of the measurement of a signal or signals from a detectable species can have direct influence upon the quality of an assay result, particularly when the result is near the limits of an assay performance.

Immunoassays typically involve the use of several assay points (e.g. vessels such as tubes) were accurate dispensing of reagents is required. Also, it is necessary to make the assumption that reactions at different assay points (e.g. in different vessels) proceed to the same degree in a given period of time even though in practice this may not be the case.

The accuracy and precision of the measurement of a signal or signals for a detectable species may be improved if absolute measurements are avoided; one way in which this may be achieved is by measuring the ratio of signals from two detectable species. This type of measurement may be termed ratiometric detection or measurement.

By way of example, two detectable species may be used and the detectable species may be selected such that the signal level of one of the detectable species may be influenced by the presence of an entity to be detected and such that the signal level of the other detectable species is not substantially influenced by the presence of the entity; this signal level may, for example, be such that it is influenced by the concentration of entity to be detected.

By way of example, the two detectable species may, in general, be chosen so as to be detectable independently of each other and so as to be such as not to interfere mutually to any unacceptable degree.

It may be possible to use more than two detectable species in some circumstances.

By way of example, the following may be considered to be advantages of ratiometric detection or measurement in accordance with the present invention:

(a) ratiometric procedures may be used, for example, to give increased precision of signal measurement which may lead to an increase in detection sensitivity;

(b) in accordance with the present invention reactions may, for example, be allowed to proceed in solution, prior to effecting a separation in accordance with the present invention; reactions in solution may be expected to proceed more quickly and efficiently than reactions involving immobilised species;

(c) the amount of first detectable species and second detectable species may, for example, be monitored at each assay point in an immunoassay and thus it is not necessary to rely on assumptions regarding these amounts (e.g. it is not necessary to assume that a "constant" amount of second detectable species is present);

(d) in view of the fact that, for example, a separation may be effected in accordance with the present invention, the present invention is not necessarily dependent upon long term stability of an immobilised detectable species.

It is to be understood that the present invention may find application in qualitative detection of an entity (e.g. an analyte species), which may also be considered to be qualitative analysis of an entity, or in quantitative detection of an entity (e.g. an analyte species) which may also be considered to be quantitative analysis (i.e. measurement or determination of an entity).

By way of example, the present invention may find application in single entity detection (e.g. single analyte species detection). By way of further example, the present invention may find application in the detection of more than one entity (i.e. in multi-entity detection (e.g. multi-analyte species detection)); thus, for example, more than one type of secondary species and more than one type of secondary species reaction partner may be used effecting multi-entity detection.

The entity to be detected may be, for example, any entity capable of undergoing a specific binding reaction. Thus, for example, an entity to be detected may itself be an analyte species. For example, an entity to be detected may be an analyte species comprising a ligand (e.g. an antigenic ligand such as a hapten). By way of further example, an entity to be detected may be an analyte species comprising an antibody.

Examples of entities which may be detected in accordance with the present invention (which entities themselves are analyte species) are:

(a) steroid hormones such as progesterone, 17α-hydroxy progesterone or estradiol (e.g. in a sample of blood, serum, saliva, urine or milk), (b) hormones such as thyroid hormones (e.g. thyroxine or triiodothyronine), (c) steroids in extracts (e.g. extracts of solids or liquids), (d) drugs such as drugs of abuse (e.g. phenobarbital) and therapeutic drugs (e.g. digoxin) (in, for example, a sample of blood, serum, saliva or urine), (e) polypeptide hormones (e.g. hCG), in, for example, a sample of blood or urine, (f) tumour markers such as marker proteins (e.g. in a sample of blood or serum), (g) protein antigens, (h) blood proteins (e.g. human serum albumin, immunoglobulins (e.g. IgG), enzyme markers or receptors), (i) marker proteins in urine resulting from kidney diseases, (j) pesticides such as insecticides, and herbicides (e.g. in a sample of water or of soil), (k) toxins (such as those extracted from feeds and food stuffs), (l) micro-organisms (e.g. viruses and bacteria), and (m) antibodies to micro-organisms.

A further example of entities which may be detected (which entities themselves comprise analyte species) are complexes of metals (e.g. strong metal complexes which may be regarded as toxic in biological terms when present in the environment). An example of a metal complex which may be detected in accordance with the present invention is methyl mercury.

By way of further example an entity to be detected may be an entity which carries or includes an analyte species. Thus, for example, the entity to be detected may be a species formed-by interaction of an analyte species and a suitable agent.

For example, where an analyte species is a metal ion the agent may be a complexing agent capable of interacting with the metal ion to form an entity (e.g. a metal ion complex) for detection.

Examples of complexing agents are chelating agents.

Examples of chelating agents are:

ethylene diamine tetra acetate (EDTA), diethylene triamine penta acetate (DTPA), cyclohexylenedinitrilo tetra acetic acid (CDTA), 1-benzyl-EDTA, derivatives of 1-benzyl-EDTA, 8-hydroxyquinoline, derivatives of 8-hydroxyquinoline, and deferoxamine.

The following are examples of metals which may be analyte species capable of being formed into an entity to be detected comprising a metal complex:

calcium ($Ca^{II}$), iron ($Fe^{II}$, $Fe^{III}$), cobalt ($Co^{II}$, $Co^{III}$), aluminium ($Al^{III}$), zinc ($Zn^{II}$), lead ($Pb^{II}$), copper ($Cu^{II}$, $Cu^{I}$), cadmium ($Cd^{II}$), vanadium ($V^{II}$, $V^{III}$), silver ($Ag^{I}$, $Ag^{II}$), mercury ($Hg^{I}$, $Hg^{II}$), indium ($In^{III}$), manganese ($Mn^{II}$), and nickel ($Ni^{II}$).

In view of the immediately foregoing disclosure it will be appreciated that the present invention may find application inter alia, in the detection of metal complex or metal ions in samples (e.g. samples of water or soil from the environment).

From the foregoing disclosure, it will be appreciated that in an embodiment of the present invention a method may include the step of forming a complex of an analyte species, said complex thus formed providing an entity to be detected.

It is to be appreciated that in accordance with the present invention an entity to be detected or an analyte species which may be formed into an entity to be detected may be initially present in any suitable sample; by way of example, an entity aqueous detected may be formed into an aqueous sample form (whatever the original nature of the sample medium in which an entity or analyte species was obtained) for subjecting to detection in accordance with the present invention.

The present invention may find application, for example, in the detection of entities to be detected, in any suitable sample. Thus, for example, samples of water, soil, living species (such as plants (e.g. vegetables) or animals) or air may provide entities to be detected, for detection in accordance with the present invention. By way of example, air-borne species may be entities to be detected and such air-borne species may be, for example, extracted from a sample of air and then subjected to detection. Examples of biological samples in which entities to be detected, may be detected in accordance with the present invention are blood, plasma, serum, urine, saliva and milk. Entities to be detected may be, for example, present in water, an aqueous preparation or a fluid extract (e.g. one prepared by solvent extraction). Entities to be detected may be, for example, haptens.

Any suitable immunoassay configuration may find application in accordance with the present invention.

The present invention may find application in, for example, heterogeneous immunoassay methods, sandwich immunoassay methods, competitive immunoassay methods, non-competitive immunoassay methods, and direct immunoassay methods.

The present invention may find application in, for example, detectable species-dependent (e.g. tracer-species-dependent) assay methods such as enzyme-immunoassay, fluoro-immunoassay, and radioimmunoassay. By way of example, the present invention may find application in antigen-labelled immunoassay methods, and antibody-labelled immunoassay methods.

By way of example, any suitable species may be associated with a detectable species in accordance with the present invention as may be required by any chosen immunoassay configuration; thus, for example, depending upon the configuration utilised a primary species comprising an antibody (e.g. anti-entity antibody) may be associated with a detectable species, or a primary species comprising an antigenic species (e.g. an authentic entity) may be associated with a detectable species, or a second antibody may be associated with a detectable species, or a secondary species carrying an auxiliary binder may be associated with a detectable species, or a secondary species comprising an auxiliary ligand may be associated with a detectable species. Where the primary species comprises an antigenic species, the antigenic species may be, for example, an antigen or a hapten.

In accordance with the present invention a first detectable species and a second detectable species may be associated with any suitable species. For example, the following combinations of species may be utilised:

(A) primary antibody/auxiliary binder, (B) primary antibody/auxiliary ligand, (C) second antibody/auxiliary binder, (D) second antibody/auxiliary ligand, (E) developing binder (as hereinbefore disclosed)/auxiliary binder, and (F) developing binder (as hereinbefore disclosed)/auxiliary ligand.

By way of example only, a number of immunoassay configurations which may find application in accordance with the present invention will now be described:

(i) In one example, the following may be utilised: a primary species comprising an antigenic species, said antigenic species comprising an authentic entity (e.g. a hapten), a first detectable species, said first detectable species being linked to the antigenic species (thus providing a labelled entity structure of an immunoassay), an antibody to the antigenic species (which antibody may be considered to be a primary species reaction partner), a secondary species comprising an auxiliary binder, said secondary species being linked to the antibody to the antigenic species, a second detectable species, said second detectable species linked to the secondary species, a secondary species reaction partner (comprising a ligand for the secondary species), and a support material, said secondary species reaction partner being attached to the support material.

By way of example, the various species, the antibody, the secondary species reaction partner and the support material, as disclosed in the immediately preceding paragraph, may be used in a competitive immunoassay. In carrying out such a competitive immunoassay the primary species comprising an antigenic species may be introduced to the antibody to the antigenic species and allowed to compete, with any entity to be detected present, for specific binding with the antibody to the antigenic species.

In the absence of an entity to be detected the antigenic species will bind with the antibody and subsequently both the first detectable species and second detectable species may be attached to the support material by using the "separation" capabilities of the combination of secondary species and secondary species reaction partner. (Thus, upon binding occurring between the secondary species and the secondary species reaction partner, the second detectable species (which is linked to the secondary species) becomes indirectly attached to the support material, and also the first detectable species becomes indirectly attached to the support material (via the antigenic species and the antibody therefor.)

The ratio of signal from the first detectable species and signal from a second detectable species may then be determined by any suitable method or methods (which may depend upon the kind of detectable species utilised).

In the presence of entity to be detected some of the antigenic species, to which is linked the first detectable species, will not be bound with the antibody since the entity will be competing with the antigenic species with respect to binding with the antibody.

Accordingly, after using the separation capabilities of the secondary species/secondary species reaction partner combination, the ratio of signals of the two detectable species will be found to be different from the situation where no entity to be detected is present; it is to be understood that this is because less of the antigenic species, which is linked to the first detectable species, will be present on the support material.

It is to be understood that as the amount of entity to be detected increases, it occupies more antibody at the expense of the antigenic species linked to the first detectable species; thus increasing entity concentrations will lead to a reduction in the amount of first detectable species retained on the support material and hence a change in the ratio of signals of first detectable species and second detectable species.

It will be appreciated that by use of "standards" containing known amounts of authentic entity, calibration curves may be constructed which may, subsequently, be used for detecting the presence of and/or the amount of entity to be detected present in "unknown" samples.

(It will be appreciated that the antibody to the antigenic species and the entity to be detected are also primary species inasmuch as they may take part in a primary immune binding reaction.)

(ii) In another example, the following may be utilised: a primary species comprising an antigenic species, said antigenic species comprising an authentic entity (e.g. a hapten), a first detectable species, said first detectable species being linked to the antigenic species (thus providing a labelled entity structure of an immunoassay), an antibody to the antigenic species (which antibody may be considered to be a primary species reaction partner), a secondary species comprising an auxiliary ligand, said secondary species being linked to the antibody to the antigenic species, a second detectable species, said second detectable species being linked to the secondary species, a secondary species reaction partner (comprising a binder for the secondary species), and a support material, said secondary species reaction partner being attached to the support material.

By way of example, the various species, the antibody, the secondary species reaction partner and the support material, as disclosed in the immediately preceding paragraph, may be used in a competitive immunoassay.

It is to be understood that such a competitive immunoassay may be carried out in a manner which is substantially as hereinbefore disclosed in relation to (i) above with the differences that the second detectable species is linked to a secondary species comprising a ligand and that the separation is effected by binding of the secondary species to a secondary species reaction partner which comprises a binder (attached to the support material).

(iii) In a further example, the following may be utilised: a primary species comprising an antibody, a first detectable species, said first detectable species being linked to the antibody, an antigenic species (said antigenic species being an authentic entity and said antigenic species being an antigenic species to the antibody), a secondary species comprising an auxiliary binder, said antigenic species (which may be considered to be a primary species reaction partner) being linked to the secondary species, a second detectable species, said second detectable species being linked to the secondary species, a secondary species reaction partner (comprising a ligand for the secondary species), and a support material, said secondary species reaction partner being attached to the support material.

By way of example, the various species, the secondary species reaction partner and the support material, as disclosed in the immediately preceding paragraph, may be used in a competitive immunoassay.

In carrying out such a competitive immunoassay the antigenic species (which is linked to the secondary species) may be introduced to the antibody and allowed to compete, with any entity to be detected which may be present, for specific binding with the primary species.

In the absence of entity to be detected the antibody will bind with the antigenic species and subsequently both the first detectable species and the second detectable species may be attached to the support material by using the "separation" capabilities of the combination of secondary species and the secondary species reaction partner. (Thus, upon binding occurring between the secondary species and the secondary species reaction partner, the second detectable species (which is linked to the secondary species) becomes indirectly attached to the support material, and also the first detectable species becomes indirectly attached to the support material (via the antibody, the antigenic species, the secondary species and the secondary species reaction partner.)

The ratio of signal from the first detectable species and signal from the second detectable species may then be determined by any suitable method or methods (which may depend upon the kind of detectable species utilised).

In the presence of entity to be detected some of the antibody will not be bound with the antigenic species (which is linked to the secondary species) since the entity will be competing with the antigenic species with respect to binding with the antibody.

Accordingly, after using the separation capabilities of the secondary species/secondary species reaction partner combination, the ratio of signals of the two detectable species will be found to be different from the situation where no entity to be detected is present; it is to be understood that this is because less of the antibody, having linked thereto the first detectable species, will be present on the support material.

It is to be understood that as the amount of entity to be detected increases, it occupies more antibody at the expense of the antigenic species (linked to the secondary species); thus increasing entity concentrations will lead to reductions in the amount of first detectable species retained on the support material and hence a change in the ratio of signals of first detectable species and second detectable species.

It will be appreciated that by use of "standards" containing known amounts of authentic entity, calibration curves may be constructed which subsequently may be used for detecting the presence of and/or determining the amount of entity to be detected present in "unknown", samples.

(iv) In a further example, the following may be utilised; a primary species comprising an antibody, a first detectable species, said first detectable species being linked to the antibody, an antigenic species (said antigenic species being an authentic entity and said antigenic species being an antigenic species for the antibody), a secondary species comprising an auxiliary ligand, said antigenic species (which may be considered to be a primary species reaction partner) being linked to the secondary species, a second detectable species, said second detectable species being linked to the secondary species, a secondary species reaction partner (comprising a binder for the secondary species), and a support material, said secondary species reaction partner being attached to the support material.

By way of example, the various species, the secondary species reaction partner and the support material, as disclosed in the immediately preceding paragraph, may be used in a competitive immunoassay.

It is to be understood that such a competitive immunoassay may be carried out in a manner which is substantially as hereinbefore disclosed in relation to (iii) above, with the differences that the second detectable species is linked to a secondary species comprising a ligand and that the separation is effected by binding of the secondary species to a secondary species reaction partner which comprises a binder (attached to the support material).

(v) In a further example, the following may be utilised: a primary species comprising a first antibody for an entity to be detected, a secondary species comprising an auxiliary binder (said secondary species being linked to the primary species), a second detectable species, said second detectable species being linked to the secondary species, a secondary species reaction partner (comprising a ligand for the secondary species), a support material, said secondary species reaction partner being attached to the support material, another antibody, which may be described as a "developing" antibody, capable of binding with an entity to be detected, and a first detectable species, said first detectable species being linked to the developing antibody.

(It is to be understood that the developing antibody may also be considered to be a "signal" antibody.)

By way of example, the various species, the secondary species reaction partner, the support material, and the developing antibody, as disclosed in the immediately preceding paragraph, may be used in a non-competitive sandwich immunoassay.

In carrying out such a non-competitive sandwich immunoassay use is made of the fact that the first antibody can undergo a specific binding reaction with an entity to be detected and the developing antibody can undergo another specific binding reaction with the entity to be detected.

Thus, in the presence of an entity to be detected, which is an antigenic species to the first antibody (which is linked to the secondary species) and an antigenic species to the developing antibody, the entity binds with the first antibody. Subsequently, the "separation" capabilities of the combination of secondary species and the secondary species reaction partner are used to attach the second detectable species to the support material. Thus, binding is arranged to occur between the secondary species and the secondary species reaction partner such that the secondary species becomes indirectly attached to the support material. Since the secondary species is linked to the first antibody and the first antibody is linked to the entity to be detected the first antibody and entity to be detected also become indirectly linked to the support material.

Subsequently the developing antibody, linked to the first detectable species, may be applied and allowed to undergo specific binding with the entity which entity is also bound to the first antibody.

Thus, the first detectable species becomes indirectly bound to the support material.

The ratio of signal from the first detectable species and signal from the second detectable species may then be determined by any suitable method or methods (which may depend upon the kind of detectable species utilised).

In the absence of entity to be detected the second detectable species will still be attached to the support material since it does not rely on the presence of the entity for its attachment.

However, in the absence of entity to be detected, the first detectable species will not become attached to the support material to any significant extent because the entity is required in order to effect the attachment of the developing antibody.

Accordingly in the absence of entity to be detected a signal may be obtained from the support material from the second detectable species thereon, but substantially no signal will be observed in respect of the first detectable species.

It will be appreciated that as the amount of entity to be detected increases the amount of first detectable species attached to the support material will-increase and thus the ratio of signals from first detectable species and second detectable species will change as the amount of first detectable species signal increases.

By the use of "standards" containing known amounts of authentic entity, calibration curves may be constructed which may subsequently be used for detecting the presence of and/or determining the amount of entity to be detected present in "unknown" samples.

It will be appreciated that the above described sequence may be varied as desired. Thus, for example, application of the developing antibody linked to the first detectable species may precede the binding between the secondary species and the secondary species binding partner.

(It will be appreciated that the first antibody may be considered to be an "immobilising" antibody in that the first antibody may be seen as serving to attach the entity to be detected to the support material (via the secondary species and the secondary species reaction partner).)

(vi) In a further example, the following may be utilised: a primary species comprising a first antibody for an entity to be detected, a secondary species comprising an auxiliary ligand (said secondary species being linked to the primary species), a second detectable species, said second detectable species being linked to the secondary species, a secondary species reaction partner (comprising a binder for the secondary species), a support material, said secondary species reaction partner being attached to the support material, another antibody, which may be described as a "developing" antibody, capable of binding with an entity to be detected, and a first detectable species, said first detectable species being linked to the developing antibody.

(It is to be understood that the developing antibody may also be considered to be a "signal" antibody.)

By way of example, the various species, the secondary species reaction partner, the support material and the developing antibody, as disclosed in the immediately preceding paragraphs, may be used in a non-competitive sandwich immunoassay.

It is to be understood that such a non-competitive sandwich immunoassay procedure may be carried out in a manner which is substantially as hereinbefore described in relation to (v) above, with the differences that the second detectable species is linked to a secondary species comprising a ligand and that the separation is effected by binding of the secondary species to a secondary species reaction partner which comprises a binder (attached to the support material).

(It will be appreciated that the first antibody may be considered to be an "immobilising" antibody in that the first antibody may be seen as serving to attach the entity to be detected to the support material (via the secondary species and the secondary species reaction partner).)

(vii) In a further example, the following may be utilised: a primary species comprising a first antibody, a second antibody (being an antibody to the first antibody), a first detectable species, said first detectable species being linked to the second antibody, an antigenic species (said antigenic species being an authentic entity and said antigenic species being an antigenic species for the primary species), a secondary species comprising an auxiliary binder, said antigenic species (which may be considered to be a primary species reaction partner) being linked to the secondary species, a second detectable species, said second detectable species being linked to the secondary species, a secondary species reaction partner (comprising a ligand for the secondary species), and a support material, said secondary species reaction partner being attached to the support material.

By way of example, the various species, the second antibody, the secondary species reaction partner and the support material, as disclosed in the immediately preceding paragraph, may be used in a competitive immunoassay.

In carrying out such a competitive immunoassay the antigenic species (which is linked to the secondary species) may be introduced to the primary species and allowed to compete, with any entity to be detected present, for specific binding with the primary species.

In the absence of entity to be detected the first antibody will bind with the antigenic species and subsequently the second detectable species may be attached to the support material by using the "separation" capabilities of the combination of secondary species and the secondary species reaction partner. (Thus, upon binding occurring between the secondary species and the secondary species reaction partner, the second detectable species (which is linked to the secondary species) becomes indirectly linked to the support material.)

On applying the second antibody (linked to the first detectable species) the second antibody binds with the first antibody so that the first detectable species also becomes indirectly attached to the support material (via, inter alia, second antibody, first antibody, antigenic species, secondary species and secondary species reaction partner).

The ratio of signal from the first detectable species and signal from the second detectable species may then be determined by any suitable method or methods (which may depend upon the kind of detectable species utilised).

In the presence of entity to be detected some of the first antibody will not be bound with the antigenic species linked to the secondary species since the entity will be competing with the antigenic species with respect to binding with the first antibody.

Accordingly, after using the separation capabilities of the secondary species/secondary species reaction partner combination, and applying the second antibody linked to the first detectable species, the ratio of signals of the two detectable species will be found to be different from the situation where no entity to be detected is present; it is to be understood that this is because less of the second antibody, having linked thereto the first detectable species, will be present on the support material.

It will be understood that as the amount of entity to be detected increases, it binds with more of the first antibody at the expense of the antigenic species which is linked to the secondary species; thus increasing entity concentrations will lead to reductions in the amount of first detectable species retained on the support material and hence to changes in the ratio of signals of first detectable species and second detectable species.

It will be appreciated that by use of "standards" containing known amounts of authentic entity, calibration curves may be constructed which subsequently may be used for detecting the presence of and/or determining the amount of entity to be detected present in "unknown" samples.

In general, the order of steps given above (i.e. primary immune binding reaction, separation and application of second antibody) may be found convenient. However, the order of the steps may be varied, if desired, to suit particular applications.

(viii) In a further example, the following may be utilised: a primary species comprising a first antibody, a second antibody (being an antibody to the primary species), a first detectable species, said first detectable species being linked to the second antibody, an antigenic species (said antigenic species being an authentic entity and said antigenic species being an antigenic species for the first antibody), a secondary species comprising an auxiliary ligand, said antigenic species (which may be considered to be a primary species reaction partner) being linked to the secondary species, a second detectable species, said second detectable species being linked to the secondary species, a secondary species reaction partner (comprising a binder for the secondary species), and a support material, said secondary species reaction partner being attached to the support material.

By way of example, the various species, the second antibody, the secondary species reaction partner and the support material, as disclosed in the immediately foregoing paragraph, may be used in a competitive immunoassay.

It is to be understood that such a competitive immunoassay may be carried out in a manner which is substantially as hereinbefore disclosed in relation to (vii) above, with the differences that the second detectable species is linked to a secondary species comprising a ligand and that separation is effected by binding of the secondary species to a secondary species reaction partner which comprises a binder (attached to the support material).

(ix) In a further example, the following may be utilised: a primary species comprising an antibody, a first detectable species, a first detectable species carrier (comprising a binder), said first detectable species carrier being linked to the first detectable species, a ligand for the first detectable species carrier said ligand being linked to the antibody, an antigenic species (said antigenic species being an authentic entity and said antigenic species being an antigenic species for the antibody), a secondary species comprising an auxiliary binder, said antigenic species (which may be considered to be a primary species reaction partner) being linked to the secondary species, a second detectable species, said second detectable species being linked to the secondary species, a secondary species reaction partner (comprising a ligand for the secondary species), and a support material, said secondary species reaction partner being attached to the support material.

The first detectable species carrier may be, for example, an antibody.

By way of example, the various species, the first detectable species carrier, the ligand for the first detectable species carrier, the secondary species reaction partner, and the support material, as disclosed in the immediately preceding paragraph, may be used in a competitive immunoassay.

It is to be understood that such a competitive immunoassay may be carried out in a manner which is substantially as hereinbefore disclosed with reference to (iv) above with the difference that the first detectable species is linked to the antibody by use of the combination of first detectable species carrier and the ligand for the first detectable species carrier rather by use of a second antibody for the antibody.

(x) In a further example, the following may be utilised: a primary species comprising an antibody, a first detectable species, a first detectable species carrier (comprising a binder), said first detectable species being linked to the first detectable species, a ligand for the first detectable species carrier said ligand being linked to the antibody, an antigenic species (said antigenic species being an authentic entity and said antigenic species being an antigenic species for the antibody), a secondary species comprising an auxiliary ligand, said antigenic species (which may be considered to be a primary species reaction partner) being linked to the secondary species, a second detectable species, said second detectable species being linked to the secondary species, a secondary species reaction partner (comprising a binder for the secondary species), and a support material, said secondary species reaction partner being attached to the support material.

The first detectable species carrier may be, for example, an antibody.

By way of example, the various species, the first detectable species carrier, the ligand for the first detectable species carrier, the secondary species reaction partner and the support material may be used in a competitive immunoassay.

It is to be understood that such a competitive immunoassay may be carried out in a manner which is substantially as hereinbefore disclosed in relation to (ix) above with the differences that the second detectable species is linked to a secondary species comprising a ligand and that the separation is effected by binding of the secondary species to a secondary species reaction partner which comprises a binder (attached to the support material).

(xi) In a further example the following may be utilised: a primary species comprising an antibody, a first detectable species, said first detectable species being linked to the antibody, an antigenic species (said antigenic species comprising an authentic entity and said antigenic species being an antigenic species for the antibody), a secondary species comprising an enzyme (said enzyme being capable of acting as secondary species and as a second detectable species), said antigenic species (which may be considered to be a primary species reaction partner) being linked to said secondary species, a secondary species reaction partner (comprising a binder for the secondary species), and a support material, said secondary species reaction partner being attached to the support material.

The secondary species reaction partner may be, for example, an antibody.

By way of example, the primary species, the first detectable species, the antigenic species, the secondary species (which is also capable of acting as a secondary species and as a second detectable species), the secondary species reaction partner, and the support material, as disclosed in the immediately preceding paragraph may be used in a competitive immunoassay.

It is to be understood that such a competitive immunoassay may be carried out in a manner which is substantially as hereinbefore disclosed in relation to (iv) above with the difference that the secondary species, in addition to acting as a secondary species, also acts as the second detectable species.

(xii) In a further example the following may be utilised: a primary species comprising an antigenic species, said antigenic species comprising an authentic entity (e.g. a hapten), a first detectable species, said antigenic species and said first detectable species being linked together (either directly or via a suitable species such as a carrier protein) thereby to provide a labelled entity structure of an immunoassay, an antibody to the antigenic species, a secondary species comprising an enzyme (said enzyme being capable of acting as a secondary species and as a second detectable species), said antibody (which may be considered to be a primary species reaction partner) being linked to said secondary species, a secondary species reaction partner (comprising a binder for the secondary species), and a support material, said secondary species reaction partner being attached to the support material.

The secondary species reaction partner may be, for example, an antibody.

By way of example, the primary species, the first detectable species, the antibody, the secondary species (which is capable of acting as a secondary species and as a second detectable species), the secondary species reaction partner and the support material, as disclosed in the immediately preceding paragraph, may be used in a competitive immunoassay.

It is to be understood that such a competitive immunoassay may be carried out in a manner which is substantially as hereinbefore disclosed in relation to (ii) above with the difference that the secondary species also acts as the second detectable species.

(xiii) In a further example, the following may be utilised: a primary species comprising an antibody, a first detectable species, said first detectable species being linked to the antibody, an antigenic species (said antigenic species comprising an authentic entity and said antigenic species being an antigenic species for the antibody), a secondary species comprising a ligand (said ligand being capable of acting as secondary species and as a second detectable species), said antigenic species (which may be considered to be a primary species reaction partner) being linked (either directly or via a suitable species such as a carrier protein) to said secondary species, a secondary species reaction partner (comprising a binder for the secondary species), and a support material, said secondary species reaction partner being attached to the support material.

The secondary species reaction partner may be, for example, an antibody.

By way of example, the primary species, the first detectable species, the antigenic species, the secondary species (which is capable of acting as a secondary species and as a second detectable species), the secondary species reaction partner and the support material, as disclosed in the immediately preceding paragraph, may be used in a competitive immunoassay.

It is to be understood that such a competitive immunoassay may be carried out in a manner which is substantially as hereinbefore disclosed in relation to (iv) above with the difference that the secondary species, in addition to acting as a secondary species, also acts as the second detectable species.

(xiv) In a further example, the following may be utilised: a primary species comprising an antigenic species, said antigenic species comprising an authentic entity (e.g. a hapten), a first detectable species, said antigenic species and said first detectable species being linked together (either directly or via a suitable species such as a carrier protein) thereby to provide a labelled entity structure of an immunoassay, an antibody to the antigenic species, a secondary species comprising a ligand (said ligand being capable of acting as secondary species and as a second detectable species), said antibody (which may be considered to be a primary species reaction partner) being linked to said secondary species, a second species reaction partner (comprising a binder (e.g. an antibody) for the secondary species), and a support material, said secondary species reaction partner being attached to the support material.

The secondary species reaction partner may be, for example, an antibody.

By way of example, the primary species, the first detectable species, the antibody, the secondary species (which is capable of acting as a secondary species and as a second detectable species), the secondary species reaction partner and the support material, as disclosed in the immediately preceding paragraph, may be used in a competitive immunoassay.

It is to be understood that such a competitive immunoassay may be carried out in a manner which is substantially as hereinbefore disclosed in relation to (ii) above with the difference that the secondary species in addition to acting as a secondary species, also acts as a second detectable species.

It is to be understood that the entity to be detected in the foregoing examples (i) to (xiv) may be an analyte species as such (examples of analyte species being hereinbefore disclosed) or an entity which carries or includes an analyte species (examples of entities being hereinbefore disclosed).

It will be understood that the links utilised in the foregoing examples (i) to (xiv) may be direct or indirect (e.g. via a carrier protein) as desired.

By way of example, it is to be understood that, optionally, a washing step or washing steps, such as those known in the field of immunological detection, may be utilised if desired in carrying out the method in accordance with the present invention.

It is also to be understood that any species or entity involved in utilising the present invention may be brought together in any suitable combination, in any suitable manner and at any time.

The term "antibody" as used in this Specification embraces whole antibody and antibody fragments such as Fab and (Fab)$_2$ and, accordingly, the term "antibodies" used herein embraces whole antibodies and antibody fragments.

According to another aspect of the present invention there is provided a sensor suitable for use in immunological detection of an entity, which sensor includes a support material, a secondary species reaction partner provided on the support material and means for effecting a ratiometric detection utilising the secondary species reaction partner, a secondary species (as hereinbefore defined), a first detectable species and a second detectable species.

According to a further aspect of the present invention there is provided a test-kit suitable for use in immunological detection of an entity to be detected which test-kit includes a secondary species (as hereinbefore defined), a first detectable species and a second detectable species.

By way of example, if desired the present invention may make use of an inactive species or a plurality of inactive species which may be activated as required to be utilised in accordance with the present invention.

Thus, for example, an inactive species or a plurality of inactive species may be such as to be reconstitutable to an active form.

An inactive form of a species may be prepared by drying and/or freeze-drying (lyophilising) so as to produce a reconstitutable reagent system or a reconstitutable reagent material.

For example, a secondary species, or a first detectable species, or a second detectable species, or a primary species or a secondary species reaction partner may be, or any of these in any suitable combination, may be prepared in a reconstitutable form (e.g. by freeze-drying) such that upon reconstitution ratiometric detection may be effected.

Reconstitution may be effected in any suitable manner, for example, by addition of a reconstituting agent such as a suitable solvent (e.g. water), or a suitable solution (e.g. an aqueous solution) or a suitable sample (e.g. an aqueous sample).

By way of further example, if desired, the present invention may make use of a "switchable" separation. Thus, for example, the present invention may make use of a first auxiliary species capable of being formed into a second auxiliary species which second auxiliary species is capable of interacting with a third species to facilitate a separation.

DETAILED DESCRIPTION OF THE PREFERRED EMBODIMENTS

The present invention will now be further described, by way of example only, as follows:

EXAMPLE 1

Preparation of Anti-analyte Species Antiserum

L-thyroxine was selected as an entity being an analyte species to illustrate, by way of example, ratiometric detection in accordance with the present invention. Accordingly it was necessary to prepare an antibody to L-thyroxine.

Thus, antiserum to L-thyroxine was raised in sheep against thyroxine-N-amidosuccinate-KLH (keyhole limpet haemocyanin) and antibody obtained in accordance with known procedures. The antibody thus obtained was purified by affinity chromatography using thyroxine-N-amidoglutaric acid-AH-Sepharose 4B (Pharmacia) as an affinity matrix. Antibody retained on the matrix was eluted with a mixture of acetonitrile (20%) and propionic acid (1%) in distilled water.

The antibody thus obtained may be considered to be a primary antibody.

EXAMPLE 2

Association of Primary Antibody with a First Detectable Species

A first detectable species was chosen, in this Example, to be 5(6) carboxyfluorescein and this was associated with the primary antibody prepared in Example 1 by use of 5(6)-carboxyfluorescein-N-hydroxysuccinimide ester.

To prepare the ester, N-hydroxysuccinimide (2.1 mmoles) and dicyclohexylcarbodiimide (2.1 mmoles) were added to 5(6)-carboxy fluorescein (2.0 mmoles) dissolved in tetrahydrofuran (40 mls) containing 1M HCl (25 µl).

The resulting reaction mixture was left in the cold (4° C.) for three days to allow formation of the ester.

5(6)-carboxyfluorescein-N-hydroxysuccinimide ester (about 500 nmoles) were reacted with purified primary antibody IgG (10 mg), prepared as in Example 1, dissolved in 0.1M NaHCO$_3$ (3 ml; pH 8.6) containing 0.1M NaCl.

The resulting fluorescein labelled primary antibody was purified by gel filtration.

EXAMPLE 3

Preparation of Antiserum to Secondary Species Reaction Partner

In the Examples, the secondary species reaction partner was chosen to be an auxiliary ligand and the auxiliary ligand was chosen to be 2-phenyl-4-quinoline carboxylic acid. Accordingly, it was necessary to prepare antibody to 2-phenyl-4-quinoline carboxylic acid; it will be appreciated that the antibody was prepared so as to act as a secondary species (in this Example an auxiliary binder being an auxiliary antibody).

Thus, an immunogen of the auxiliary ligand 2-phenyl-4-quinoline carboxylic acid was prepared by reacting the N-hydroxysuccinimide ester (80 µmoles) of the ligand with a mixture of KLH (keyhole limpet haemocyanin) and BSA (bovine serum albumin) (50 mg in 3% NaHCO$_3$ (7 ml; pH 8.6)).

The immunogen was dialysed and subsequently used to raise antiserum in animals (rabbits) in accordance with known procedures.

Antibodies to the auxiliary ligand was obtained from the antiserum by affinity chromatography using auxiliary ligand-AH-Sepharose-4B as an affinity chromatography matrix.

Antibody retained on the matrix was eluted with a mixture of acetonitrile (20%) and propionic acid (1%) in distilled water.

EXAMPLE 4

Conjugation of Secondary Species to Analyte Derivative and Association of Second Detectable Species with the Secondary Species Antibody (i.e. secondary species) prepared as in Example 3 was conjugated with analyte derivative to form a secondary species-authentic entity conjugate (in this Example a secondary species-authentic analyte species conjugate) and a second detectable species was also associated with the antibody.

Thyroxine-N-amidoglutaric acid-N-hydroxysuccinimide ester was prepared by adding N-hydroxysuccinimide (0.27 mmoles) and dicyclohexylcarbodiimide (0.27 mmoles) to a solution of thyroxine-N-amidoglutaric acid (0.25 mmoles) in dimethyl formamide (7 ml). The resulting reaction mixture was left in the cold (4° C.) for three days to allow formation of the ester.

About 300 nmoles of the ester thus prepared were reacted for 4 hours at room temperature with secondary species being antibody (12 mg) as prepared in Example 3, dissolved in 0.1M NaHCO$_3$ (3 ml; pH 8.6) containing 0.1M NaCl. Subsequently, 7-amino-4-methyl-coumarin-3-propionic acid-N-hydroxysuccinimide ester (about 600 nmoles) were added and left to react at 4° C. for 16 hours to introduce second detectable species. The resulting conjugate of secondary species, authentic analyte species and second detectable species was purified by gel filtration.

The 7-amino-4-methyl-coumarin-3-propionic acid-N-hydroxysuccinimide ester was prepared by adding N-hydroxysuccinimide (1.2 mmoles) and dicyclohexylzarbodiimide (1.2 mmoles) to 7-amino-4-methyl-coumarin-3-propionic acid (1.0 mmole) dissolved in a mixture of dioxane (10 ml) and methanol (5 ml).

The resulting reaction mixture was left in the cold (4°C.) for five days to allow formation of the ester.

EXAMPLE 5

Providing Support Material with Secondary Species Reaction Partner

As was hereinbefore described in Example 3 the ligand 2-phenyl-4-quinoline carboxylic acid was chosen as an example of a secondary species reaction partner; a coating conjugate was prepared by conjugating the ligand to ovalbumin.

Thus, the ligand 2-phenyl-4-quinoline carboxylic acid was converted to an N-hydroxysuccinimide ester by reacting the ligand (2 mmoles) in dimethylformamide (25 ml) with N-hydroxysuccinimide (2.1 mmoles) and dicyclohexylcarbodiimide (2.1 mmoles) for 3 days at 4° C.

Ovalbumin (25 mg) dissolved in 3% NaHCO$_3$ (5 ml; pH 8.6) and dimethylsulphoxide (DMSO) (1 ml) was reacted with about 16 µmoles of ester prepared as immediately hereinbefore disclosed. After 16 hours at room temperature the resulting material was dialysed for 3 days and treated with 0.3% Norrit A activated charcoal so that a purified ligand-ovalbumin conjugate was obtained.

In order to provide secondary specific reaction panner on a support material, solutions of the ligand-ovalbumin conjugate (4 µg/ml in 0.05M NaHCO$_3$ solution) were used to coat internal surfaces of polystyrene immunoassay tubes (75×12 mm) using 1 ml volumes.

Tubes were emptied after coating and excess sites were blocked with horse haemoglobin (0.5 mg/ml). The tubes thus prepared could be stored dry in the cold for long periods.

EXAMPLE 6

Assay of Analyte Species

A range of standard solution was prepared in 50 mm Tris-HCl (pH 8.0) with 0.1M NaCl, 0.1% NaN$_3$ and rhodamine B base (50 µg/ml). The standard solutions ranged from a "zero standard" solution containing no analyte species up to a standard solution containing 10 ng/ml thyroxine.

To duplicate assay tubes, prepared as in Example 5, 800 µl of the standard solutions were added.

Subsequently, 100 µl of fluorescein labelled primary antibody (prepared as in Example 5), appropriately diluted, was added to the tubes.

The tubes were shaken to mix the contents thereof and left to incubate for 20 min after which 100 µl of the conjugate of the secondary species, authentic analyte species and second detectable species (as prepared in Example 4) was added to the tubes.

After incubation for 10 min the tubes were emptied and washed 3 times and any material which had been retained by attachment to the tubes was brought into solution by desorption with 1 ml of Na$_2$CO$_3$ solution (pH 10.0) containing 20% acetonitrile.

Fluorescence intensities of fluorescein ($\lambda_{abs}$=490 nm, $\lambda_{max}$=510 nm) and of 7-amino-4-methyl-coumarin ($\lambda_{abs}$=360 nm, $\lambda_{max}$=450 nm) were measured in a fluorimeter (Perkin Elmer LS5).

A calibration graph for thyroxine was constructed by plotting the ratio of fluorescein fluorescence intensity to 7-amino-4-methyl-coumarin fluorescence intensity; this represented a typical competitive immunoassay calibration graph.

It was observed that fluorescein fluorescence intensity decreased as analyte species (thyroxine) concentration increased from 0 to maximum whereas 7-amino-4-methyl-coumarin fluorescence intensity remained largely unchanged.

Hence, a calibration graph for the analyte species (thyroxine) constructed by plotting the ratio of fluorescein fluorescence intensity to 7-amino-4-methyl-coumarin fluorescence intensity gave a typical immunoassay curve in which ratio values decreased as the analyte species concentration increased.

I claim:

1. In a competitive assay method for immunological detection in a sample of the presence or concentration of an analyte species, wherein (a) a primary species comprises an analyte analog; (b) the primary species provides or is associated with a first detectable species; (c) a primary species reaction partner is provided which is capable of undergoing a specific binding reaction in a primary immune reaction mixture with the analyte species, if present, or with the analyte analog; (d) both the sample and the primary species are exposed to and incubated with the primary species reaction partner; (e) means are provided for separating the primary species from the reaction mixture; and (f) a signal from the first detectable species is detected by a signal-detecting means, the improvement comprising:

(i) causing a second detectable species to become associated with a support material via a secondary species and a secondary species reaction partner, said secondary species (A) being a species which does not itself undergo a specific binding reaction with the analyte species or with the analyte analog, (B) providing or being associated with the second detectable species, (C) undergoing a specific binding reaction with the secondary species reaction partner which is provided on or by, or associated with, the support material, and (D) being or becoming linked to the primary species reaction partner; and (ii) if the analyte analog becomes bound to the primary species reaction partner, causing the first detectable species to become associated with the support material via linkage of the primary species reaction partner to the secondary species, with signals from said first and second detectable species being detectable by the signal detection means independently of each other and without interference one with another, whereby quantitative comparison of the respective signal levels detected from the first and second detectable species enables ratiometric detection of the analyte species.

2. In a competitive assay method for immunological detection in a sample of the presence or concentration of an analyte species, wherein (a) a primary species provides or is associated with a first detectable species; (b) a primary species reaction partner is provided which comprises an analyte analog; (c) the primary species is capable of undergoing a specific binding reaction in a primary immune reaction mixture with the analyte species, if present, or with the primary species reaction partner; (d) both the sample and the primary species reaction partner are exposed to and incubated with the primary species; (e) means are provided for separating the primary species reaction partner from the reaction mixture; and (f) a signal from said first detectable species is detected by a signal-detecting means, the improvement comprising:

(i) causing a second detectable species to become associated with a support material via a secondary species and a secondary species reaction partner, said secondary species (A) being a species which does not itself undergo a specific binding reaction with the analyte species or with the analyte analog, (B) providing or being associated with the second detectable species, (C) undergoing a specific binding reaction with the secondary species reaction partner which is provided on or by, or associated with, the support material, and (D) being or becoming linked to the primary species reaction partner; and (ii) If the primary species becomes bound to the analyte analog, causing the first detectable species to become associated with the support material via linkage of the primary species reaction partner to the secondary species, with signals from said first and second detectable species being detectable by the signal detection means independently of each other and without interference one with another, whereby quantitative comparison of the respective signal levels detected from the first and second detectable species enables ratiometric detection of the analytic species.

3. In a non-competitive assay method for immunological detection in a sample of the presence or concentration of an analyte species, wherein (a) a primary species is exposed to and incubated with the sample, (b) the primary species undergoes a specific binding reaction with the analyte species, if present in the sample, in a primary immune reaction mixture, (c) a developing species undergoes a specific binding reaction with the analyte species, if present in the sample; (d) the developing species provides or is associated with a first detectable species, (e) means are provided for separating the primary species from the reaction mixture, and (f) a signal from said first detectable species is detected by a signal-detecting means, the improvement comprising:

(i) causing a second detectable species to become associated with a support material via a second species and a secondary species reaction partner, said secondary species (A) being a species which does not itself undergo a specific binding reaction with the analyte species, (B) providing or being associated with the second detectable species, (C) undergoing a specific binding reaction with the secondary species reaction partner which is provided on or by, or associated with, the support material, and (D) capable of becoming linked to the primary species; and (ii) if the analyte species is present in the sample, causing the first detectable species to become associated with the support material via specific binding of the developing species to the analyte species, specific binding of the analyte species to the primary species and linkage of the primary species to the secondary species, with signals from said first and second detectable species being detectable by the signal detection means independently of each other and without interference one with another, whereby quantitative comparison of the respective signal levels detected from the first and second detectable species enables ratiometric detection of the analyte species.

4. A test kit suitable for use in immunological detection in a sample of the presence or concentration of an analyte species, said test kit comprising:

(a) a primary species, said primary species or a reaction partner therefor capable of undergoing a specific binding reaction with the analyte species;

(b) a first detectable species provided (i) on or by, or associated with, said primary species, or (ii) on or by, or associated with, a developing species capable of undergoing a specific binding reaction with the analyte species;

(c) a secondary species being a species which does not itself undergo a specific binding interaction with the analyte species;

(d) a second detectable species provided on or by, or associated with, said secondary species; and (e) a secondary species reaction partner provided on or by, or capable of becoming associated with, a support material, whereby when the test kit is in use the second detectable species becomes associated with the support material via specific binding of the secondary species to the secondary species reaction partner, and the first detectable species is capable of becoming associated with the support material via linkage of the primary species to the secondary species, with signals from said first and second detectable species being detectable by the signal detection means independently of each other and without interference one with another.

5. The improvement as claimed in claims 1, 2 or 3 wherein the primary species is a primary antibody or a ligand.

6. The improvement as claimed in claims 1, 2 or 3 wherein the secondary species is an antibody for an antigenic species.

7. The improvement as claimed in claim 6 wherein the antibody is selected from the group consisting of anti-2,4 dinitrophenol antibody, anti-fluorescein antibody, anti-digitoxin antibody, anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3.3.0] octane-2-carboxylic acid antibody, anti-endo-bicyclo [2.2.2] oct-5-ene-2,3-dicarboxylic anhydride antibody, anti-N-[4-(4-aminobenzyl) phenyl]-5-norbornene-2,3-dicarboximide antibody, and anti-[IR-(2-endo, 3-exo)]-3-hydroxy-4,7,7-trimethyl bicyclo [2.2.1] heptane-2-acetic acid antibody.

8. The improvement as claimed in claims 1, 2 or 3 wherein the secondary species is a binder for a non-antigenic ligand.

9. The improvement as claimed in claim 8 wherein the binder is avidin.

10. The improvement as claimed in claims 1, 2 or 3 wherein the secondary species is an antigenic ligand.

11. The improvement as claimed in claim 10 wherein the antigenic ligand is selected from the group consisting of 2,4 dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyl-3-quinaldine carboxylic acid, cis-bicyclo [3.3.0] octane-2-carboxylic acid, endo-bicyclo [2.2.2] oct-5-ene-2,3-dicarboxylic anhydride, N-[4-(4-aminobenzyl) phenyl]-5-norbornene-2,3-dicarboximide, and [IR-(2-endo, 3-exo)]-3-hydroxy-4,7,7-trimethyl bicyclo [2.2.1] heptane-2-acetic acid.

12. The improvement as claimed in claims 1, 2 or 3 wherein the secondary species is a non-antigenic ligand.

13. The improvement as claimed in claim 12 wherein the ligand is biotin.

14. The improvement as claimed in claims 1, 2 or 3 wherein the secondary species is a bifunctional antibody.

15. The improvement as claimed in claims 1, 2 or 3 wherein the secondary species reaction partner is selected from the group consisting of anti-2,4 dinitrophenol antibody, anti-fluorescein antibody, anti-digitoxin antibody, anti-coumarin antibody, anti-cibacron blue antibody, anti-2-(4-aminophenyl)-6-methyl benzothiazole-hemiglutarate antibody, anti-camphorcarboxylic acid antibody, anti-4-amino-benzo-15-crown-5 antibody, anti-carboxyfluorescein antibody, anti-3-methyl-1-adamantane acetic acid antibody, anti-2-phenyl-4-quinoline carboxylic acid antibody, anti-xanthine-9-carboxyamide-glycine-glycine antibody, anti-4-hydroxy-7-trifluoromethyl-3-quinaldine carboxylic acid antibody, anti-cis-bicyclo [3,3,0] octane-2-carboxylic acid antibody, anti-endo-bicyclo [2,2,2] oct-5-ene-2,3-dicarboxylic anhydride antibody, anti-N-[4-(4-aminobenzyl) phenyl]-5-norbornene-2,3-dicarboximide antibody, anti-[IR-(2-endo, 3-exo)]-3-hydroxy-4,7,7-trimethyl bicyclo [2.2.1] heptane-2-acetic acid antibody, 2,4-dinitrophenol, fluorescein, digitoxin, coumarin, cibacron blue, 2-(4-aminophenyl)-6-methyl benzothiazole-hemiglutarate, camphorcarboxylic acid, 4-amino-benzo-15-crown-5, carboxyfluorescein, 3-methyl-1-adamantane acetic acid, 2-phenyl-4-quinoline carboxylic acid, xanthine-9-carboxyamide-glycine-glycine, 4-hydroxy-7-trifluoromethyt-3-quinaldine carboxylic acid, cis-bicyclo [3,3,0] octane-2-carboxylic acid, endo-bicyclo [2,2,2] oct-5-ene-2,3-dicarboxylic anhydride, N-[4-(4-aminobenzyl) phenyl]-5-norbornene-2,3-dicarboximide, and [IR-(2-endo, 3-exo)]-3-hydroxy-4,7,7-trimethyl bicyclo [2,2,1] heptane-2-acetic acid.

16. The improvemement as claimed in claims 1, 2 or 3 wherein the support material is a reaction vessel wall, an insoluble polysaccharide, a microparticle, polystyrene, cross-linked dextran, an insoluble polymer structure, a glass surface, a derivatised silica surface, a polymer attached to a surface, a magnetisable particle, nylon or a polyamide.

17. A method as claimed in claims 1, 2 or 3 wherein the support material is in the form of a carrier which may be moved from a sample application means for applying a sample to the carrier, to a detection means thereby to allow successive detection of analyte species.

18. The improvement as claimed in claims 1 2 or wherein the primary species reaction partner is an antibody or an antigenic species.

19. The improvement as claimed in claims 1, 2 or 3 wherein the first detectable species is selected from the group consisting of an enzyme, a species capable of giving a fluorescent signal, a chemiluminescent compound, a bioluminescent compound, a radioisotope, a dye, a ligand, a polymer of a ligand, a binder and a polymer of a binder.

20. The improvement as claimed in claim 19 wherein the enzyme is selected from the group consisting of alkaline phosphatase, β-galactosidase and horse-radish peroxidase.

21. The improvement as claimed in claim 19 wherein the species capable of giving a fluorescent signal is a fluorophore or a polymeric fluorophore.

22. The improvement as claimed in claim 21 wherein the fluorophore is selected from the group consisting of a fluorescein, a coumarin and rhodamine.

23. The improvement as claimed in claims 1, 2 or 3 wherein the second detectable species is selected from the group consisting of an enzyme, a species capable of giving a fluorescent signal, a chemiluminescent compound, a bioluminescent compound, a radioisotope, a dye, a ligand, a polymer of a ligand, a binder and a polymer of a binder.

24. The improvement as claimed in claim 23 wherein the second detectable species (a) is selected from the group consisting of a ligand, a polymer of a ligand, a binder and a polymer of a binder, and (b) has a tracer species associated therewith.

25. The improvement as claimed in claim 24 wherein the tracer species is selected from the group consisting of an enzyme, a fluorophore, a chemiluminescent compound, a bioluminescent compound, a radioisotope and a dye.

26. The improvement as claimed in claims 1, 2 or 3 wherein the analyte species is selected from the group consisting of a steroid hormone, a thyroid hormone, a steroid in an extract, a drug, a polypeptide hormone, a protein antigen, a tumour marker, a blood protein, a marker protein, a pesticide, a toxin, a micro-organism, an antibody to a micro-organism, and a metal complex.

27. The improvement as claimed in claim 26 wherein the metal complex is methyl mercury.

28. The improvement as claimed in claim 26 wherein the analyte species is a metal ion.

29. The improvement as claimed in claims 1, 2 or 3 wherein the method for immunological detection is designed to detect more than one analyte species.

30. The improvement as claimed in claims 1, 2 or 3 wherein the secondary species, the first detectable species, the second detectable species, the primary species or the secondary species reaction partner are prepared in reconstitutable form.

31. A method as claimed in claims 1, 2 or 3 wherein one species selected from the group consisting of the secondary species and the secondary species reaction partner is not capable of undergoing a specific binding reaction with the other species of said group, but may be converted to a species which is capable of undergoing a specific binding reaction with said other species.

* * * * *